United States Patent
Fung et al.

(10) Patent No.: US 7,432,356 B2
(45) Date of Patent: Oct. 7, 2008

(54) COMPLEMENT PATHWAY INHIBITORS BINDING TO C5 AND C5A WITHOUT PREVENTING FORMATION OF C5B

(75) Inventors: Michael Fung, Houston, TX (US); Meisheng Lu, Houston, TX (US); William N. C. Sun, Shanghai (CN); Cecily R. Y. Sun, Shanghai (CN)

(73) Assignee: Genentech, Inc., South San Francisco, CA (US)

( * ) Notice: Subject to any disclaimer, the term of this patent is extended or adjusted under 35 U.S.C. 154(b) by 125 days.

(21) Appl. No.: 10/222,464

(22) Filed: Aug. 17, 2002

(65) Prior Publication Data

US 2003/0129187 A1 Jul. 10, 2003

Related U.S. Application Data

(60) Provisional application No. 60/313,137, filed on Aug. 17, 2001.

(51) Int. Cl.
*C07K 16/44* (2006.01)
*G01N 33/53* (2006.01)

(52) U.S. Cl. ............ 530/387.1; 530/387.3; 530/388.25; 435/7.1

(58) Field of Classification Search .................. 435/7.1, 435/337, 326, 346; 424/145.1, 141.1, 809; 530/388.25, 387.1, 387.3
See application file for complete search history.

(56) References Cited

U.S. PATENT DOCUMENTS 5,256,766 A * 10/1993 Coughlin .................... 530/327

FOREIGN PATENT DOCUMENTS

WO WO 01/015731 A1 3/2001

OTHER PUBLICATIONS

Amsterdam, EA et al. Am. J. Physiol.-Heart and Circ. Physiol. [1995] 268:H448-H457.*
Güssow, D. (Meth. Enzymology [1991] 203:99-117.*
Johnson, RJ et al. J. Immunol. [1997] 138(11):3856-3862.*
Ames, RS et al. J. Immunol. [1994] 152:4572-4581.*
Larrick et al., Infection and Immunity, 55(8):1867-1872 (1987).
Communication of a Notice of Opposition dated Jan. 31, 2008.
Notice of Opposition to a European Patent dated Jan. 22, 2008 with Annex I and II.
Klos, A. et al. (1988) Jul. 22. "Detection of native human complement components C3 and C5 and their primary activation peptides C3a and C5a (anaphylatoxic peptides) by ELISAs with monoclonal antibodies." in J. Immunol. Methods 111(2): pp. 241-252.
Stevens, J. et al. (1986), "Effects of anti-C5a antibodies on the adult respiratory distress syndrome in septic primates." J. clin. Invest. 77: pp. 1812-1816.
Oppermann, M. et al. (1991), "A sensitive enzyme immunoassay for the quantitation of human C5a/C5a(desArg) anaphylatoxin using a monoclonal antibody with specificity for a neoepitope." Complement Inflamm. 8: pp. 13-24.
Mulligan, M. et al. (1986), "Requirement and role of C5a in acute lung inflammatory injury in rats." J. Clin. Invest. 98(2): pp. 503-512.
Rinder, C. et al. (1995), "Blockade of C5a and C5b-9 generation inhibits leukocyte and platelet activation during extracorporeal circulation." J. Clin. Invest. 96: pp. 1564-1572.
Kolb, W. et al., (1975), "The membrane attack mechanism of complement. Isolation and subunit composition of the C5b-9 complex." J. Exp. Med. 1975: 141(4) pp. 724-735.
Makrides, S. (1998), "Therapeutic inhibition of the complement system." Pharmocol. Revs. 50(1): pp. 59-87.
Datasheet for Abcam antibody [557] ab11876.
Print Out enquiries from Abcam website.
Kola, A. et al. (1996), "Epitope mapping of a C5a neutralizing mAb using a combined approach of phage display, synthetic peptides and site-directed mutagenesis." Immunotechnology 2: pp. 115-126.
Hartmann, H. et al., (1993), "Insulin-like growth factor II is involved in the proliferation control of medulloblastoma and its cerebellar precursor cells." J. Immunol. Methods 166: pp. 35-44.
Takeda, J. et al. (1987), "Rapid and simple measurement of human C5a-des-Arg level in plasma or serum using monoclonal antibodies." J. Immunol. Methods 101: pp. 265-270.
Schultze, M. & Gotze, O. (1996), "A Sensitive ELISA for the Quantitation of Human C5a in Blood Plasma Using a Monoclonal Antibody." Complement 3: pp. 25-39.
Alberts et al., Molecular Biology of the Cell, (1983), "How Cells are Studied" and "The Immune System." Garland Publishing: pp. 182-183 and 965-966.

* cited by examiner

*Primary Examiner*—David A. Saunders
*Assistant Examiner*—F. Pierre VanderVegt
(74) *Attorney, Agent, or Firm*—Jones Day

(57) ABSTRACT

The invention relates to inhibitors that bind to C5 and C5a, but which do not prevent the activation of C5 and do not prevent formation of or inhibit the activity of C5b. One example of such an inhibitor molecule is the monoclonal antibody designated MAb137-26, which binds to a shared epitope of human C5 and C5a. These inhibitors may be used to inhibit the activity of C5a in treating diseases and conditions mediated by excessive or uncontrolled production of C5a. The inhibitor molecules are also useful for diagnostic detection of the presence/absence or amount of C5 or C5a.

12 Claims, 11 Drawing Sheets

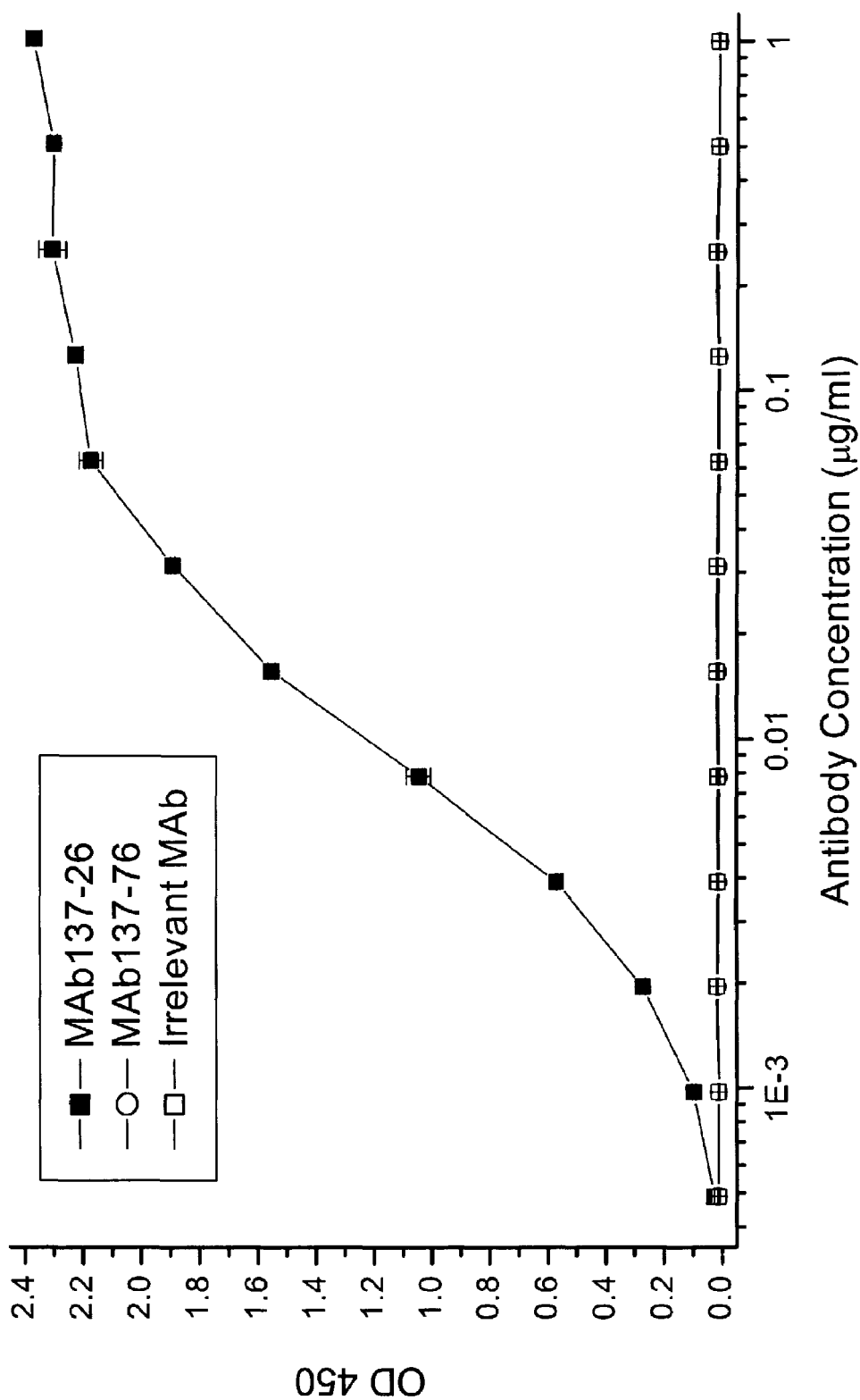
Fig. 1 Reactivity of MAb137-26 with C5a in ELISA

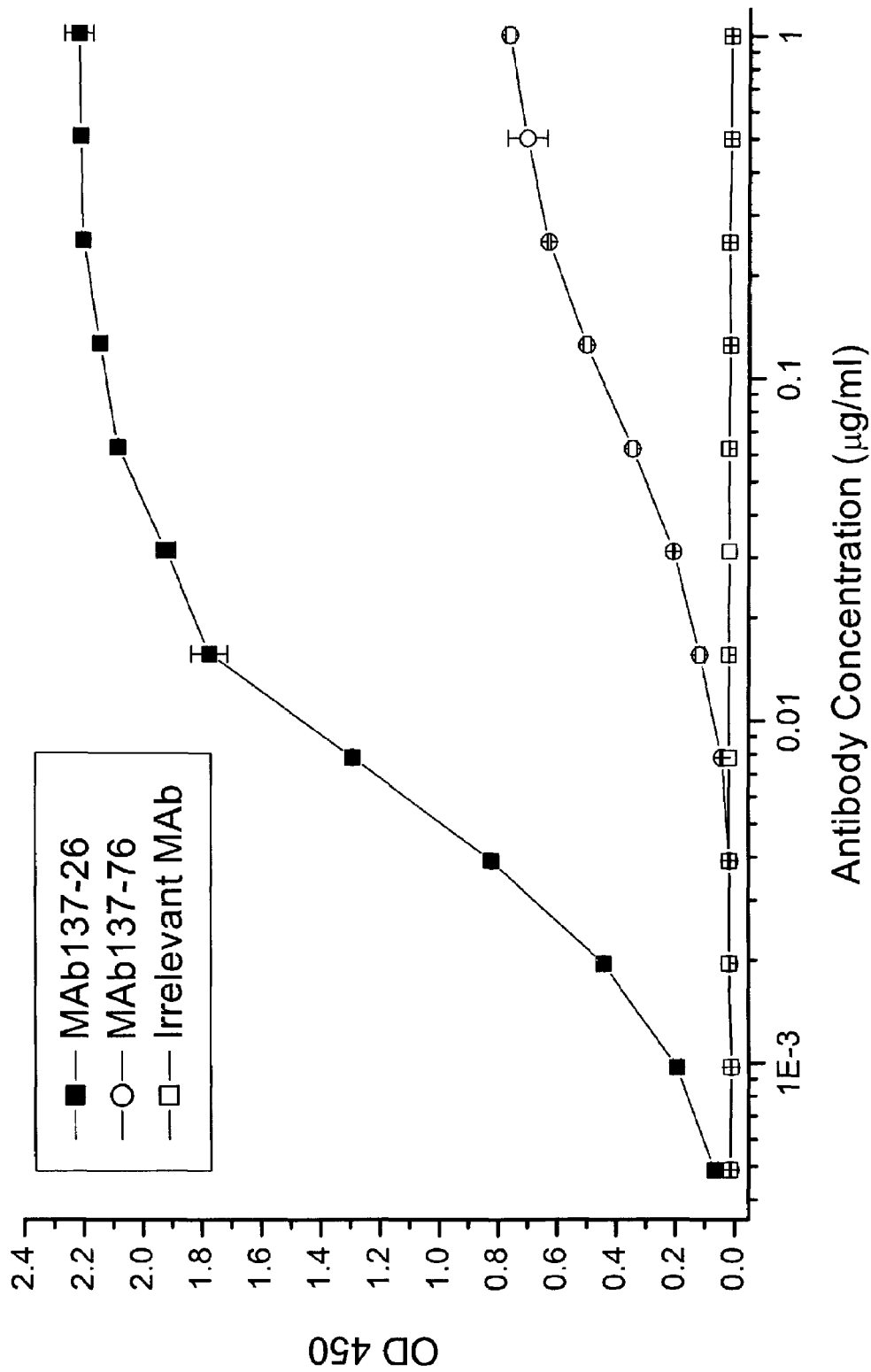
Fig. 2 Reactivity of MAb137-26 with C5 in ELISA

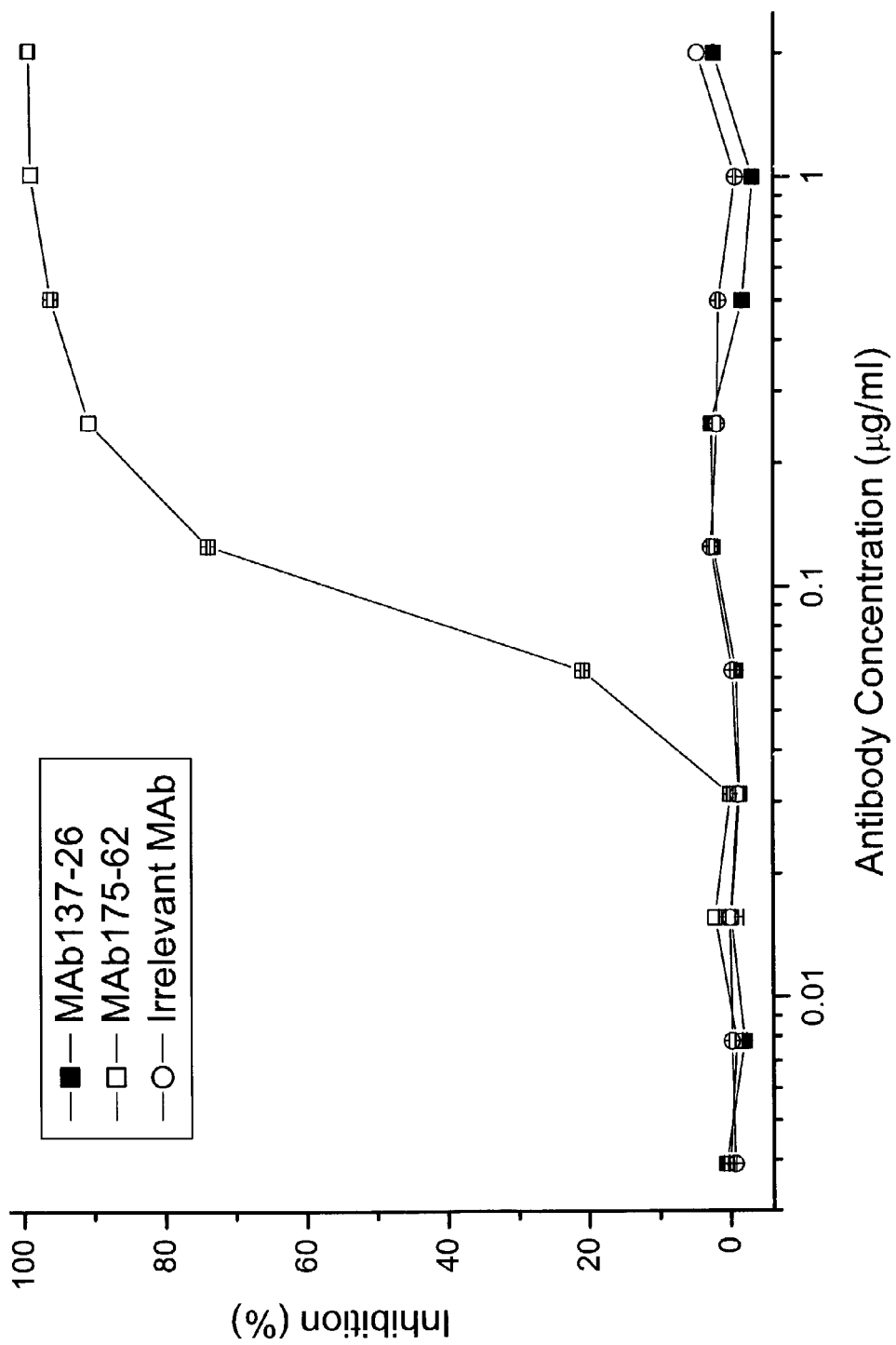

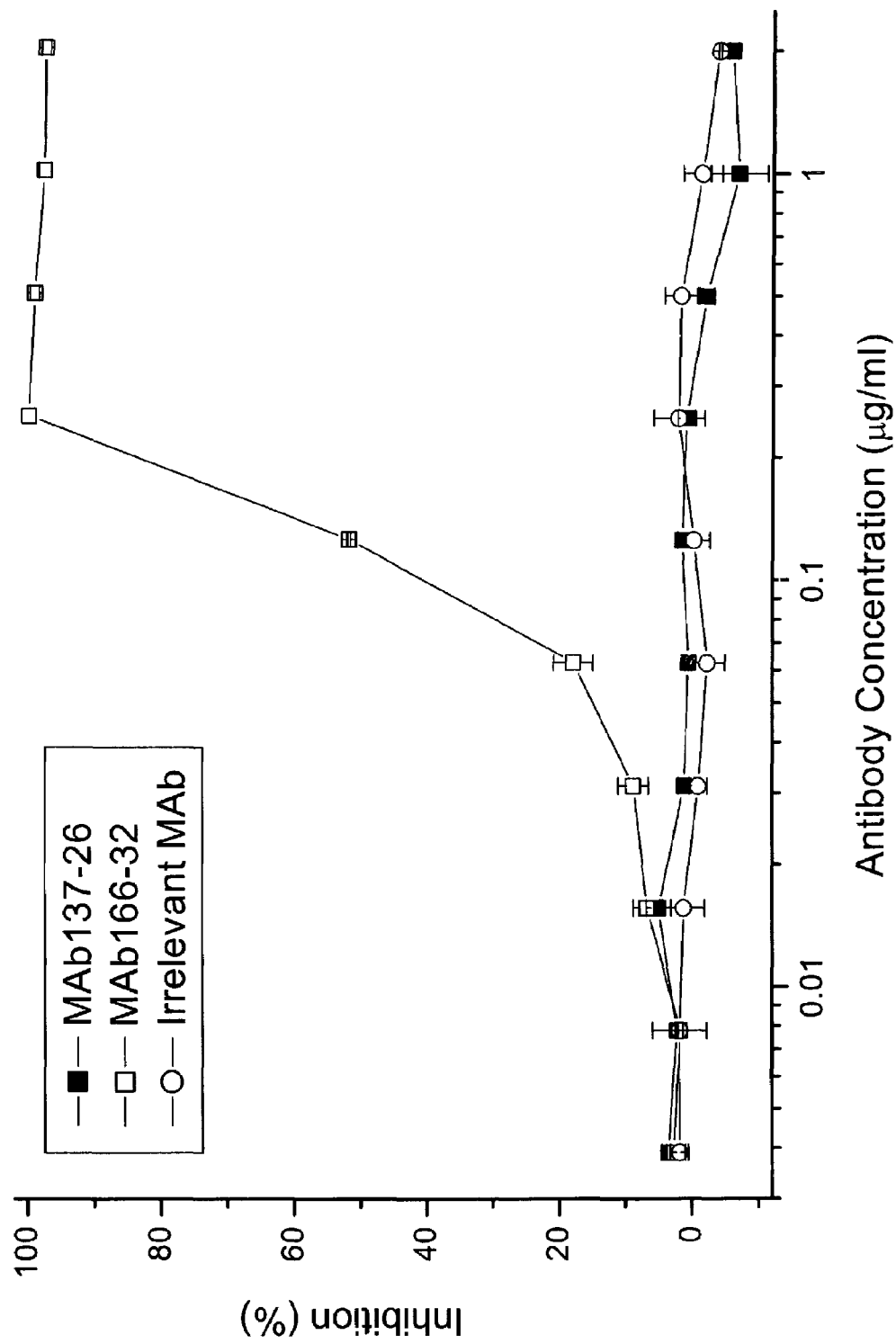
Fig. 4 No Inhibition of Complement AP Hemolysis by MAb137-26

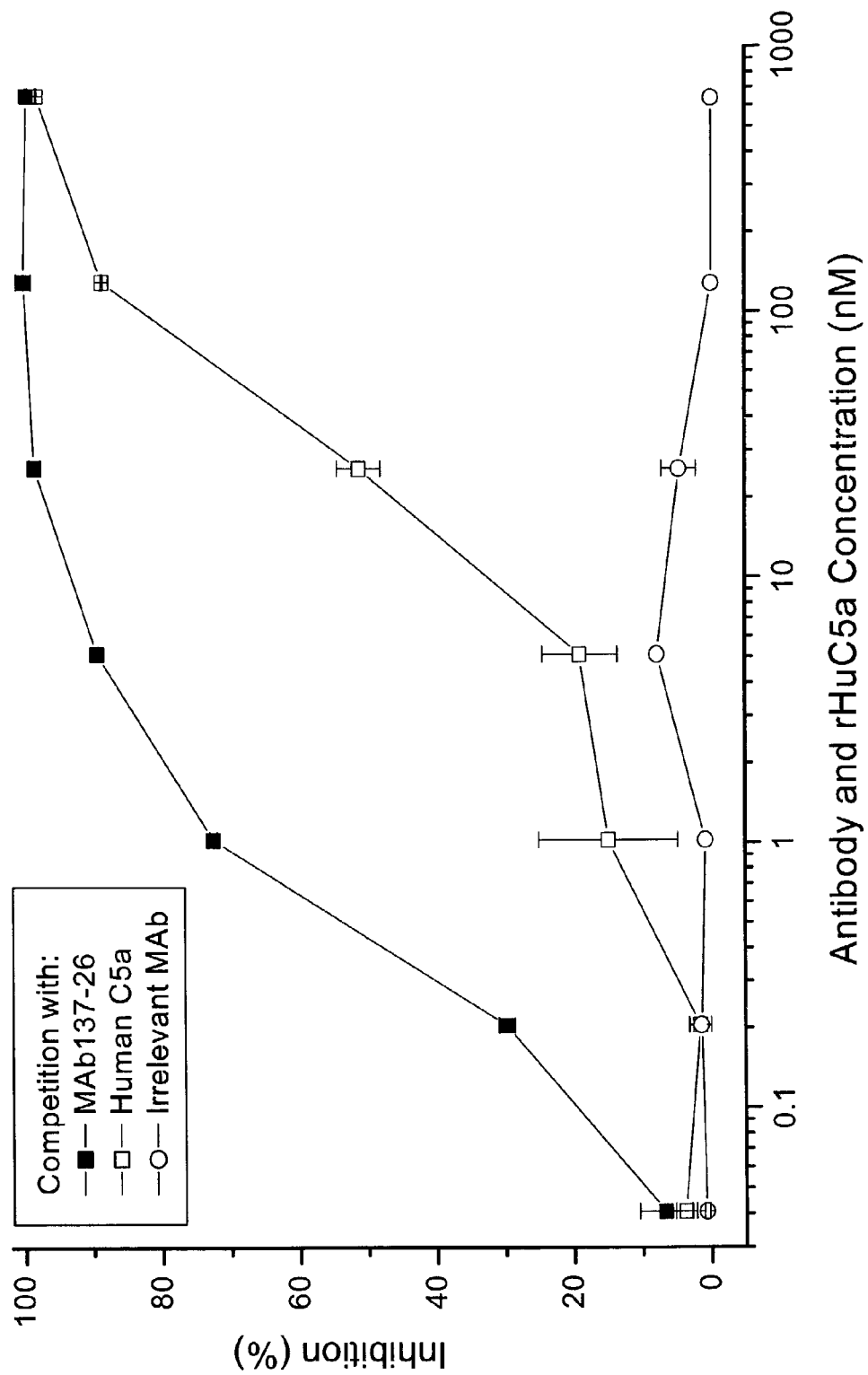
Fig. 5 Inhibition of $^{125}$I-C5a Binding to Human Neutrophils by MAb137-26

Fig. 6 Binding epitope of MAb137-26 on human C5a

N-TLQKKIEEIAAKYKHSVVKKCCYDGACVNNDETC<u>EQRAARISLGPR</u>CIKAFTECCVVASQ

LRANISHKDMQLGR –C

| Peptide | Reactivity of MAb137-26 |
|---|---|
| NNDETCEQRAAR | - |
| ETCEQRAARISL | + |
| EQRAARISLGPR | ++++ |
| AARISLGPRCIK | +++ |
| ISLGPRCIKAFT | ++ |
| GPRCIKAFTECC | - |

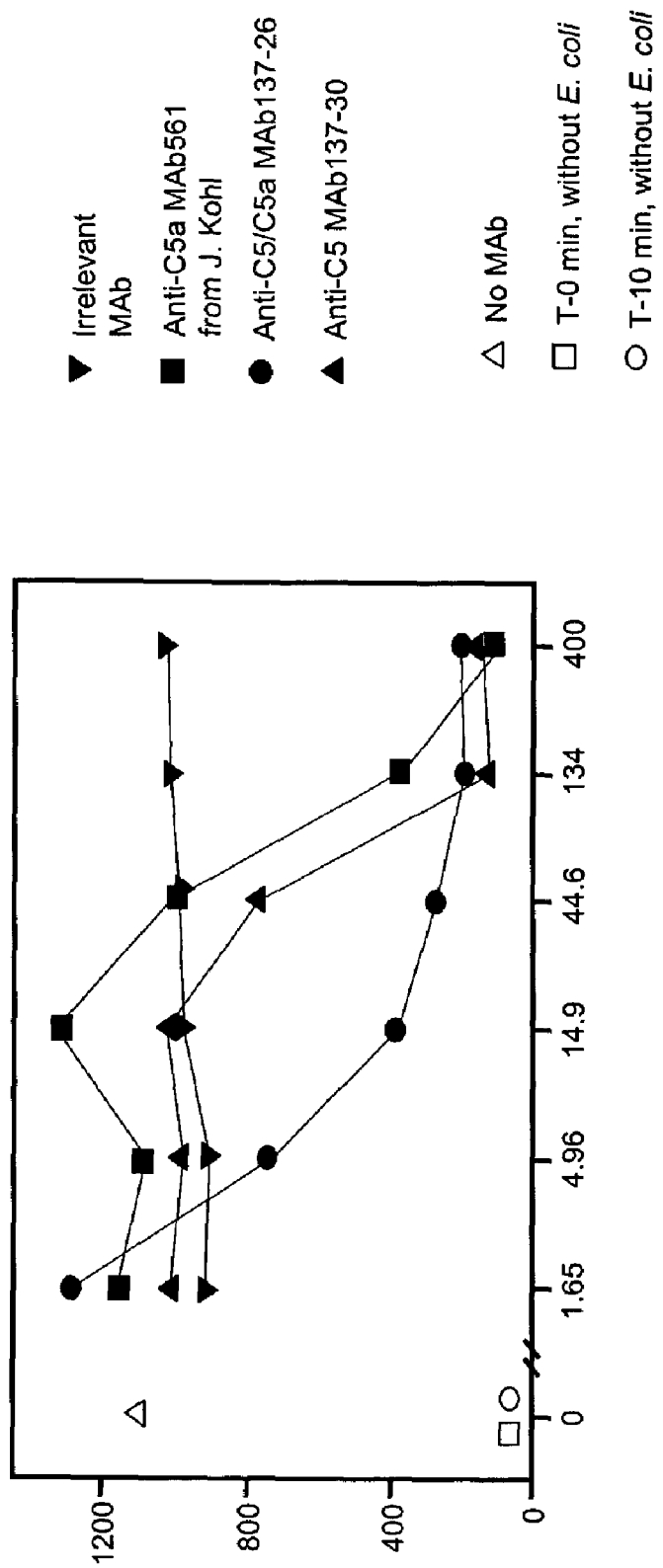
*Figure 7A Anti-C5/C5a MAb137-26 inhibits CD11b expression on human neutrophils stimulated by E. coli in a whole blood model*

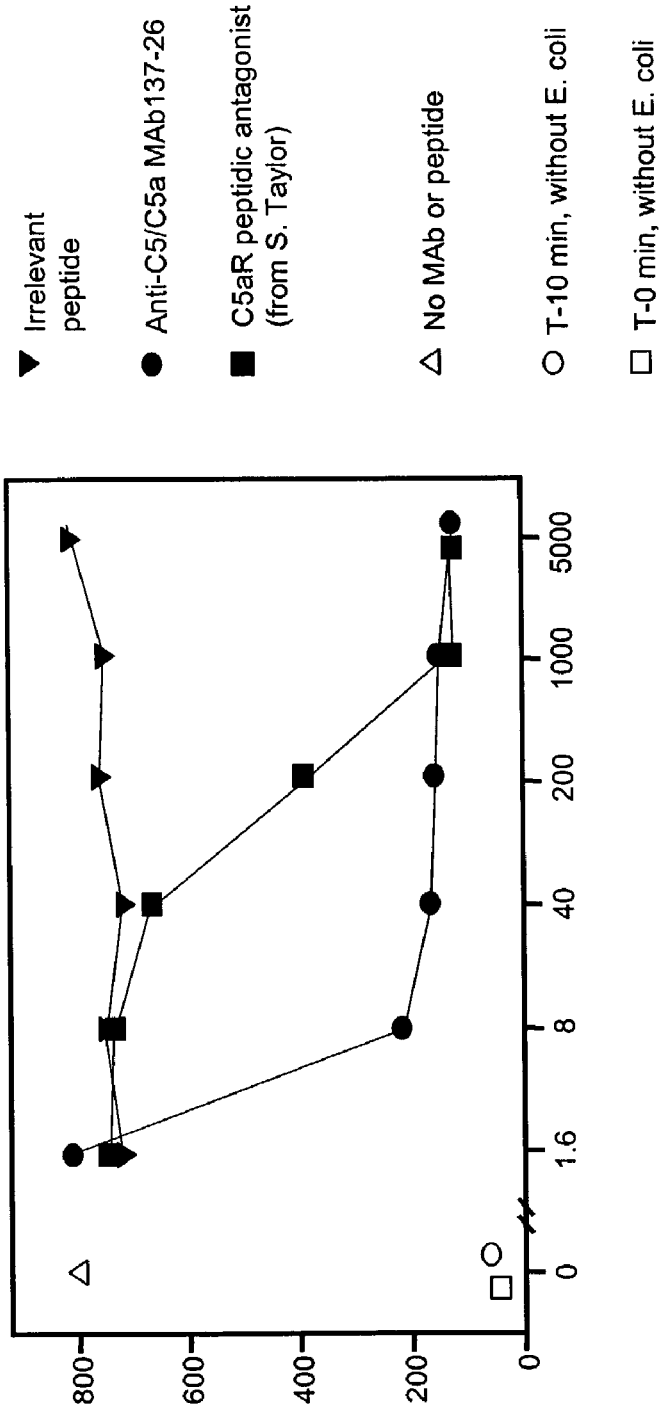
Figure 7B Anti-C5/C5a MAb137-26 inhibits CD11b expression on human neutrophils stimulated by E. coli in a whole blood model

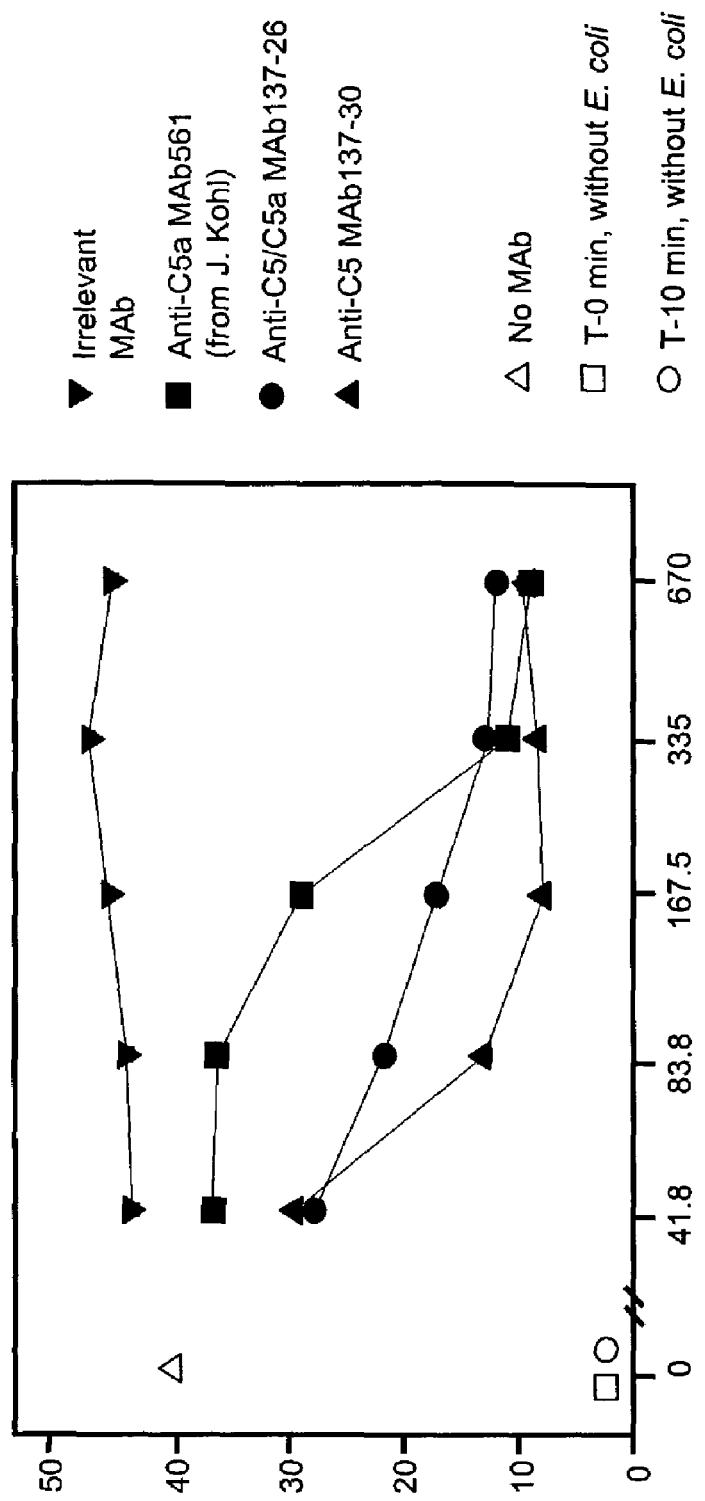
Figure 7C Anti-C5/C5a inhibits oxidative burst of human neutrophils stimulated by E. coli in a whole blood model

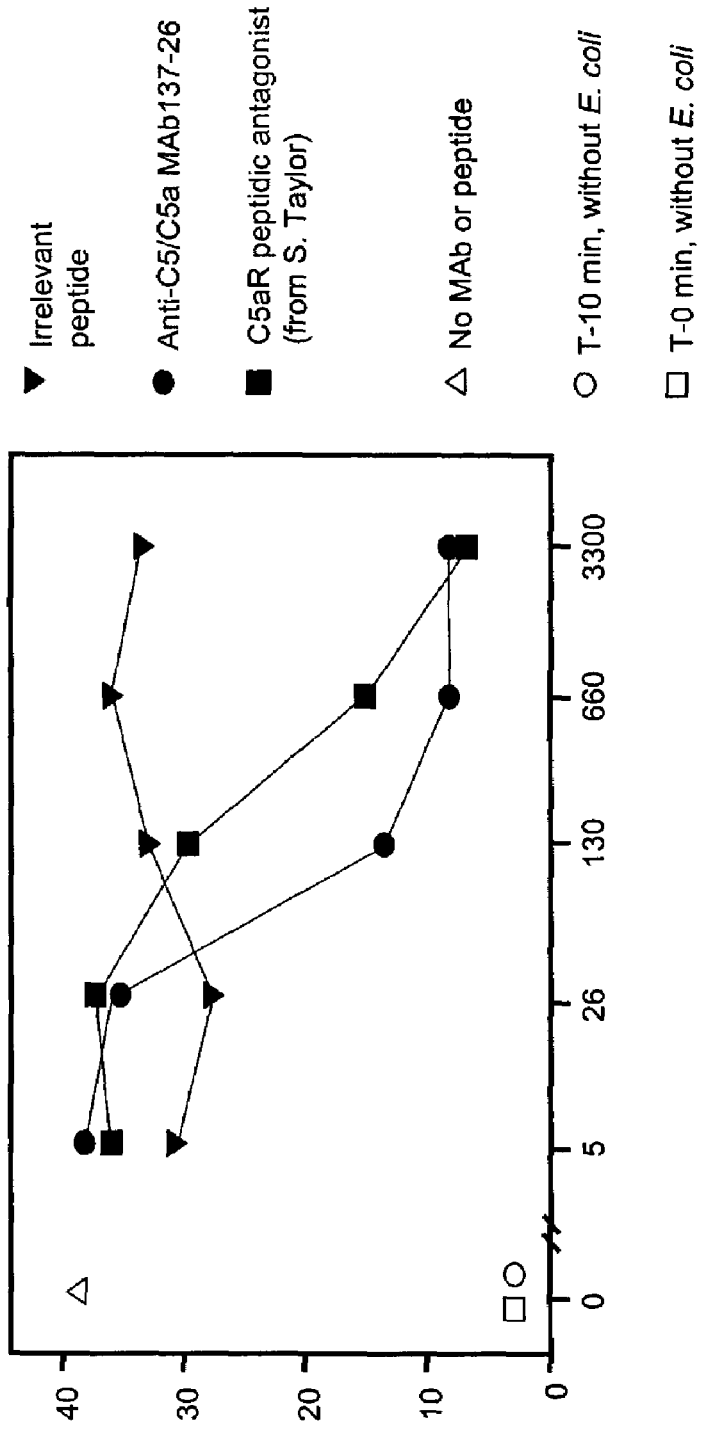
Figure 7D Anti-C5/C5a MAb137-26 inhibits oxidative burst of human neutrophils stimulated by E. coli in a whole blood model

COMPLEMENT PATHWAY INHIBITORS BINDING TO C5 AND C5A WITHOUT PREVENTING FORMATION OF C5B

CROSS-REFERENCE TO RELATED APPLICATIONS

This application claims priority to U.S. Provisional Application No. 60/313,137, filed Aug. 17, 2001, and is incorporated herein by reference.

FIELD OF THE INVENTION

This invention relates to inflammation inhibitors which bind to complement C5 and C5a without inhibiting the formation of C5b and C5b-9 membrane attack complexes (MAC).

BACKGROUND OF THE INVENTION

The complement system plays a central role in the clearance of immune complexes and in immune responses to infectious agents, foreign antigens, virusinfected cells and tumor cells. However, inappropriate or excessive activation of the complement system can lead to harmful, and even potentially life-threatening, consequences due to severe inflammation and resulting tissue destruction. These consequences are clinically manifested in various disorders including septic shock, myocardial as well as intestinal ischemia/reperfusion injury, graft rejection, organ failure, nephritis, pathological inflammation and autoimmune diseases. Sepsis, for example, is a major cause of mortality resulting in over 200,000 deaths per year in the United States alone. Despite the major advances in the past several years in the treatment of serious infections, the incidence and mortality from sepsis continues to rise. Therefore, inhibition of excessive or uncontrolled activation of the complement cascade could provide clinical benefit to patients with such diseases and conditions.

The complement system is composed of a group of proteins that are normally present in the serum in an inactive state. Activation of the complement system encompasses mainly two distinct pathways, designated the classical and the alternative pathways (V. M. Holers, In *Clinical Immunology: Principles and Practice*, ed. R. R. Rich, Mosby Press; 1996, 363-391). The classical pathway is a calcium/magnesium-dependent cascade, which is normally activated by the formation of antigen-antibody complexes. It can also be activated in an antibody-independent manner by the binding of C-reactive protein, complexed with ligand, and by many pathogens including gram-negative bacteria. The alternative pathway is a magnesium-dependent cascade which is activated by deposition and activation of C3 on certain susceptible surfaces (e.g. cell wall polysaccharides of yeast and bacteria, and certain biopolymer materials).

Recent studies have shown that complement can also be activated through the lectin pathway, which involves the initial binding of mannose-binding lectin and the subsequent activation of C2 and C4, which are common to the classical pathway (Matsushita, M. et al., *J. Exp. Med.* 176: 1497-1502 (1992); Suankratay, C. et al., *J. Immunol.* 160: 3006-3013 (1998)). Accumulating evidence indicates that the alternative pathway participates in the amplification of the activity of both the classical pathway and the lectin pathway (Suankratay, C., ibid; Farries, T. C. et al., *Mol. Immunol.* 27: 1155-1161(1990)). Activation of the complement pathway generates biologically active fragments of complement proteins, e.g. C3a, C4a and C5a anaphylatoxins and C5b-9 membrane attack complexes (MAC), which mediate inflammatory responses through involvement of leukocyte chemotaxis, activation of macrophages, neutrophils, platelets, mast cells and endothelial cells, increased vascular permeability, cytolysis, and tissue injury.

Complement C5a is one of the most potent proinflammatory mediators of the complement system. C5a is the activated form of C5. Complement C5 (190 kD, molecular weight) is present in human serum at approximately 80 µg/ml (Kohler, P. F. et al., *J. Immunol.* 99: 1211-1216 (1967)). It is composed of two polypeptide chains, α and β, with approximate molecular weights of 115 kD and 75 kD, respectively (Tack, B. F. et al., *Biochemistry* 18: 1490-1497 (1979)). Biosynthesized as a single-chain pro-molecule, C5 is enzymatically cleaved into a two-chain structure during processing and secretion. After cleavage, the two chains are held together by at least one disulphide bond as well as noncovalent interactions (Ooi, Y. M. et al., *J. Immunol.* 124: 2494-2498(1980)).

Primary amino acid structures of human and murine C5 were obtained from cDNA sequencing data (Wetsel, R. A. et al., *Biochemistry* 27: 1474-1482 (1988); Haviland, D. L. et al., *J. Immunol.*146: 362-368 (1991); Wetsel, R. A. et al, *Biochemistry* 26: 737-743 (1987)). The deduced amino acid sequence of precursor human pre-pro-C5 has 1676 amino acids. The α- and β-chains of mature C5 have 999 and 655 amino acids, respectively. C5 is glycosylated in the C5 α-chain, in particular the asparagine at residue 64.

C5 is cleaved into the C5a and C5b fragments during activation of the complement pathways. The convertase enzymes responsible for C5 activation are multi-subunit complexes of C4b, C2a, and C3b for the classical pathway and of $(C3b)_2$, Bb, and P for the alternative pathway (Goldlust, M. B. et al., *J. Immunol.* 113: 998-1007 (1974); Schreiber, R. D. et al, *Proc. Natl. Acad. Sci.* 75: 3948-3952 (1978)). C5 is activated by cleavage at position 74-75 (Arg-Leu) in the α-chain. After activation, the 11.2 kD, 74 amino acid peptide C5a from the amino-terminus portion of the α-chain is released. This C5a peptide shares similar anaphylatoxin properties with those exhibited by C3a, but is 100 times more potent, on a molar basis, in eliciting inflammatory responses. Both C5a and C3a are potent stimulators of neutrophils and monocytes (Schindler, R. et al., *Blood* 76: 1631-1638 (1990); Haeffner-Cavaillon, N. et al., *J. Immunol.* 138: 794-700 (1987); Cavaillon, J. M. et al., *Eur. J. Immunol.* 20: 253-257 (1990)). Furthermore, C3a receptor was recently shown to be important for protection against endotoxin-induced shock in a mouse model (Kildsgaard, J. et al., *J. Immunol.* 165: 5406-5409 (2000)).

In addition to its anaphylatoxic properties, C5a induces chemotactic migration of neutrophils (Ward, P. A. et al., *J. Immunol.* 102: 93-99 (1969)), eosinophils (Kay, A. B. et al., *Immunol.* 24: 969-976 (1973)), basophils (Lett-Brown, M. A. et al., *J. Immunol.* 117: 246-252 1976)), and monocytes (Snyderman, R. et al., *Proc. Soc. Exp. Biol. Med.* 138: 387-390 1971)). The activity of C5a is regulated by the plasma enzyme carboxypeptidase N (E.C. 3.4.12.7) that removes the carboxy-terminal arginine from C5a forming the C5a des Arg derivative (Goetzl, E. J. et al., *J. Clin. Invest.* 53: 591-599 (1974)). On a molar basis, human C5a des Arg exhibits only 1% of the anaphylactic activity (Gerard, C. et al., *Proc. Natl. Acad. Sci.* 78: 1833-1837 (1981)) and polymorphonuclear chemotactic activity as unmodified C5a (Chenoweth, D. E. et al., *Mol Immunol.* 17: 151-161 (1980)). Both C5a and C5b-9 activate endothelial cells to express adhesion molecules essential for sequestration of activated leukocytes, which mediate tissue inflammation and injury (Foreman, K. E. et al., *J. Clin. Invest.* 94: 1147-1155 (1994); Foreman, K. E. et al., Inflammation 20: 1-9 (1996); Rollins, S. A. et al., *Transplantation* 69: 1959-1967 (2000)). C5a also mediates inflammatory reactions by causing smooth muscle contraction, increasing vascular permeability, inducing basophil and mast cell degranulation and inducing release of lysosomal proteases and oxidative free radicals (Gerard, C. et al., *Ann. Rev. Immunol.* 12: 775-808 (1994)). Furthermore, C5a modulates the hepatic acute-phase gene expression and augments the overall immune response by increasing the production of TNFα, IL-1β, IL-6, and IL-8 (Lambris, J. D. et al., In: *The Human Complement System in Health and Disease*, Volanakis, J. E. ed., Marcel Dekker, New York, pp. 83-118).

The human C5a receptor (C5aR) has been cloned (Gerard, N. P. et al., *Nature* 349: 614-617 (1991); Boulay, F. et al., *Biochemistry* 30: 2993-2999 (1991)). It belongs to a superfamily of seven-transmembrane-domain, G protein-coupled receptors. C5aR is expressed on neutrophils, monocytes, basophils, eosinophils, hepatocytes, lung smooth muscle and endothelial cells, and renal glomerular tissues (Van-Epps, D. E. et al., *J. Immunol.* 132: 2862-2867 (1984); Haviland, D. L. et al., *J. Immunol.* 154:1861-1869 (1995); Wetsel, R. A., *Immunol. Lett.* 44: 183-187 (1995); Buchner, R. R. et al., *J. Immunol.* 155: 308-315 (1995); Chenoweth, D. E. et al., *Proc. Natl. Acad. Sci.* 75: 3943-3947 (1978); Zwirner, J. et al., *Mol. Immunol.* 36:877-884 (1999)). The ligand-binding site of C5aR is complex and consists of at least two physically separable binding domains. One binds the C5a amino terminus (amino acids 1-20) and disulfide-linked core (amino acids 21-61), while the second binds the C5a carboxy-terminal end (amino acids 62-74) (Wetsel, R. A., *Curr. Opin. Immunol.* 7: 48-53 (1995)).

C5a plays important roles in inflammation and tissue injury. In cardiopulmonary bypass and hemodialysis, C5a is formed as a result of activation of the alternative complement pathway when human blood makes contact with the artificial surface of the heart-lung machine or kidney dialysis machine (Howard, R. J. et al., *Arch. Surg.* 123: 1496-1501 (1988); Kirklin, J. K. et al., *J. Cardiovasc. Surg.* 86: 845-857 (1983); Craddock, P. R. et al., *N. Engl. J. Med.* 296: 769-774 (1977)). C5a causes increased capillary permeability and edema, bronchoconstriction, pulmonary vasoconstriction, leukocyte and platelet activation and infiltration to tissues, in particular the lung (Czermak, B. J. et al., *J. Leukoc. Biol.* 64: 40-48 (1998)). Administration of an anti-C5a monoclonal antibody was shown to reduce cardiopulmonary bypass and cardioplegia-induced coronary endothelial dysfunction (Tofukuji, M. et al., *J. Thorac. Cardiovasc. Surg.* 116: 1060-1068 (1998)).

C5a is also involved in acute respiratory distress syndrome (ARDS) and multiple organ failure (MOF) (Hack, C. E. et al., *Am. J. Med.* 1989: 86: 20-26; Hammerschmidt DE et al. *Lancet* 1980; 1: 947-949; Heideman M. et al. *J. Trauma* 1984; 4: 1038-1043). C5a augments monocyte production of two important pro-inflammatory cytokines, TNFα and IL-1. C5a has also been shown to play an important role in the development of tissue injury, and particularly pulmonary injury, in animal models of septic shock. (Smedegard G et al. *Am. J. Pathol.* 1989; 135: 489-497). In sepsis models using rats, pigs and non-human primates, anti-C5a antibodies administered to the animals before treatment with endotoxin or *E. coli* resulted in decreased tissue injury, as well as decreased production of IL-6 (Smedegard, G. et al., *Am. J. Pathol.* 135: 489-497 (1989); Hopken, U. et al., *Eur. J. Immunol.* 26: 1103-1109 (1996); Stevens, J. H. et al., *J. Clin. Invest.* 77: 1812-1816 (1986)). More importantly, blockade of C5a with anti-C5a polyclonal antibodies has been shown to significantly improve survival rates in a caecal ligation/puncture model of sepsis in rats (Czermak, B. J. et al., *Nat. Med.* 5: 788-792 (1999)). This model shares many aspects of the clinical manifestation of sepsis in humans. (Parker, S. J. et al., *Br. J. Surg.* 88: 22-30 (2001)). In the same sepsis model, anti-C5a antibodies were shown to inhibit apoptosis of thymocytes (Guo, R. F. et al., *J. Clin. Invest.* 106: 1271-1280 2000)) and prevent MOF (Huber-Lang, M. et al., *J. Immunol.* 166: 1193-1199 (2001)). Anti-C5a antibodies were also protective in a cobra venom factor model of lung injury in rats, and in immune complex-induced lung injury (Mulligan, M. S. et al. *J. Clin. Invest.* 98: 503-512 (1996)). The importance of C5a in immune complex-mediated lung injury was later confirmed in mice (Bozic, C. R. et al., *Science* 26: 1103-1109 (1996)).

C5a is found to be a major mediator in myocardial ischemia-reperfusion injury. Complement depletion reduced myocardial infarct size in mice (Weisman, H. F. et al., *Science* 249: 146-151 (1990)), and treatment with anti-C5a antibodies reduced injury in a rat model of hindlimb ischemia-reperfusion (Bless, N. M. et al., *Am. J. Physiol.* 276: L57-L63 (1999)). Reperfusion injury during myocardial infarction was also markedly reduced in pigs that were retreated with a monoclonal anti-C5a IgG (Amsterdam, E. A. et al., *Am. J. Physiol.* 268:H448-H457 (1995)). A recombinant human C5aR antagonist reduces infarct size in a porcine model of surgical revascularization (Riley, R. D. et al., *J. Thorac. Cardiovasc. Surg.* 120: 350-358 (2000)).

Complement levels are elevated in patients with rheumatoid arthritis and systemic lupus erythematosus. C5a levels correlate with the severity of the disease state (Jose, P. J. et al., *Ann. Rheum. Dis.* 49: 747-752 (1989); Porcel, J. M. et al., *Clin. Immunol. Immunopathol.* 74: 283-288 (1995)). Therefore, inhibition of C5a and/or C5a receptor (C5aR) could be useful in treating these chronic diseases.

C5aR expression is upregulated on reactive astrocytes, microglia, and endothelial cells in an inflamed human central nervous system (Gasque, P. et al., *Am. J. Pathol.* 150: 31-41 (1997)). C5a might be involved in neurodegenerative diseases, such as Alzheimer disease (Mukherjee, P. et al., *J. Neuroimmunol.* 105: 124-130 (2000)). Activation of neuronal C5aR may induce apoptosis (Farkas I et al. *J. Physiol.* 1998; 507: 679-687). Therefore, inhibition of C5a and/or C5aR could also be useful in treating neurodegenerative diseases.

Psoriasis is now known to be a T cell-mediated disease (Gottlieb, E. L. et al., *Nat. Med.* 1: 442-447 (1995)). However, neutrophils and mast cells may also be involved in the pathogenesis of the disease (Terui, T. et al., *Exp. Dermatol.* 9: 1-10; 2000); Werfel, T. et al., *Arch. Dermatol. Res.* 289: 83-86 (1997)). High levels of C5a des Arg are found in psoriatic scales, indicating that complement activation is involved. T cells and neutrophils are chemo-attracted by C5a (Nataf, S. et al., *J. Immunol.* 162: 4018-4023 (1999); Tsuji, R. F. et al., *J. Immunol.* 165: 1588-1598 (2000); Cavaillon, J. M. et al., *Eur. J. Immunol.* 20: 253-257 (1990)). Therefore C5a could be an important therapeutic target for treatment of psoriasis.

Immunoglobulin G-containing immune complexes (IC) contribute to the pathophysiology in a number of autoimmune diseases, such as systemic lupus erthyematosus, rheumatoid arthritis, Goodpasture's syndrome, and hypersensitivity pneumonitis (Madaio, M. P., *Semin. Nephrol.* 19: 48-56 (1999); Korganow, A. S. et al., *Immunity* 10: 451-459 (1999); Bolten, W. K., *Kidney Int.* 50: 1754-1760 (1996); Ando, M. et al., *Curr. Opin. Pulm. Med.* 3: 391-399 (1997)). The classical animal model for the inflammatory response in these IC diseases is the Arthus reaction, which features the infiltration of polymorphonuclear cells, hemorrhage, and plasma exudation (Arthus, M., *C.R. Soc. Biol.* 55: 817-824 (1903)). Recent studies show that C5aR deficient mice are protected from tissue injury induced by IC (Kohl, J. et al., *Mol. Immunol.* 36: 893-903 (1999); Baumann, U. et al., *J. Immunol.* 164: 1065-1070 (2000)). The results are consistent with the observation that a small peptidic anti-C5aR antagonist inhibits the inflammatory response caused by IC deposition (Strachan, A. J. et al., *J. Immunol.* 164: 6560-6565 (2000)). Together with its receptor, C5a plays an important role in the pathogenesis of IC diseases. Inhibitors of C5a and C5aR could be useful to treat these diseases.

WO01/15731A1 discusses compositions and methods of treatment of sepsis using antibodies to C5a. These antibodies react only with the N-terminal region of the C5a peptide and do not cross-react with C5.

W086/05692 discusses the treatment of adult respiratory distress syndrome (ARDS) with an antibody specific for C5a or the des Arg derivative thereof. It also discloses the treatment of sepsis by administering this antibody. This antibody was produced in response to the C5a des Arg derivative because it is more immunogenic, but will elicit antibodies cross reactive with C5a. U.S. Pat. No. 5,853,722 discusses anti-C5 antibodies that block the activation of C5 and thus, the formation of C5a and C5b.

U.S. Pat. No. 6,074,642 discusses the use of anti-C5 antibodies to treat glomerulonephritis. These antibodies also block the generation of C5a and C5b, inhibiting the effect of both C5a and the formation of C5b-9. U.S. Pat. No. 5,562,904 discusses anti-C5 antibodies that completely block the formation of MAC.

In other discussions of anti-C5 antibodies, the antibodies disclosed block activation of C5 and its cleavage to form C5a and C5b (Vakeva, A. P. et al., *Circulation* 97:2259-2267 (1998); Thomas, T. C. et al., *Mol. Immunol.* 33:1389-1401 (1996); Wang, Y. et al., *Proc Natl Acad Sci.* 93:8563-8568 (1996); Kroshus, T. et al., *Transplantation* 60:1194-1202 (1995); Frei, Y. et al., *Mol. Cell Probes* 1:141-149 (1987)).

Monoclonal antibodies cross-reactive with C5, C5a, or C5a des Arg have been reported (Schulze, M. et al., *Complement* 3: 25-39 (1986); Takeda, J. et al., *J. Immunol. Meth.* 101: 265-270 (1987); Inoue, K., *Complement Inflamm.* 6: 219-222 (1989). It has also been reported that monoclonal antibodies cross-reactive with C5 and C5a inhibited C5a-mediated ATP release from guinea pig platelets (Klos, A. et al., *J. Immunol. Meth.* 111: 241-252 (1988); Oppermann, M. et al., *Complement Inflamm.* 8: 13-24 (1991)).

SUMMARY OF THE INVENTION

C5 activation normally results in cleavage of C5 to C5a and C5b. The inhibitor molecules of the present invention bind to C5 and C5a with high affinity, do not inhibit C5 activation, and do not prevent the formation of or inhibit the activity of C5b. One example of such an inhibitor is the monoclonal antibody designated MAb 137-26, which binds to a shared epitope on human C5 and C5a. The hybridoma that produces the monoclonal antibody 137-26 has been deposited at the American Type Culture Collection, 10801 University Blvd., Manassas, Va. 20110-2209, under Accession No. PTA-3650 on Aug. 17, 2001.

The inhibitor molecules of the invention also include: (i) other antibodies or fragments thereof, peptides, oligonucleotides, or peptidomimetics that bind to C5 and C5a with high affinity, but do not inhibit C5 activation, and do not prevent the formation of or inhibit the activity of C5b, or (ii) any antibody that binds to the same epitope as the monoclonal antibody 137-26. Antibody fragments include Fab, F(ab')$_2$, Fv, or single chain Fv, and monoclonal antibodies and fragments of the invention include chimeric, DeImmunized™, humanized or human antibodies and fragments, and other forms acceptable for human use. The inhibitor molecules may be included as part of a pharmaceutical composition.

The inhibitor molecules of the invention are useful for treatment of diseases and conditions involving excessive or uncontrolled production of C5a, or for diagnostic use in detecting the presence of, or quantitation, C5a.

BRIEF DESCRIPTION OF THE FIGURES

FIG. 1 shows the binding of MAb 137-26 (anti-C5a, closed squares) and MAb 137-76 (anti-C5 β-chain, open circles) to purified human C5a in ELISA. An isotype-matched irrelevant monoclonal antibody was used as negative control. The Y-axis represents the reactivity of the MAbs with C5a expressed as optical density (OD) at 450 nm and the X-axis represents the concentration of the MAbs. MAb 137-26 reacted with human C5a, whereas MAb 137-76 and the irrelevant control antibody did not.

FIG. 2 shows the binding of MAb 137-26 (closed squares) and MAb 137-76 (open circles) to purified human C5 in ELISA. An isotype-matched irrelevant monoclonal antibody was used as negative control. The Y-axis represents the reactivity of the MAbs with C5 expressed as optical density (OD) at 450 nm and the X-axis represents the concentration of the monoclonal antibodies. Both MAb 137-26 and MAb 137-76 reacted with human C5, whereas the irrelevant antibody did not.

FIG. 3 shows the inability of anti-C5a MAb 137-26 to inhibit complement-mediated hemolysis of sensitized chicken red blood cells via the classical pathway (CP). Anti-C2 MAb 175-62 effectively inhibited the hemolysis. An isotype-matched irrelevant monoclonal antibody had no effect. The Y-axis represents the percentage of hemolysis inhibition, as further described in the text. The X-axis represents the concentration of the monoclonal antibodies.

FIG. 4 shows the inability of anti-C5a MAb 137-26 to inhibit complement-mediated hemolysis of rabbit red blood cells via the alternative pathway (AP). Anti-factor D MAb 166-32 effectively inhibited the hemolysis. An isotype-matched irrelevant monoclonal antibody had no effect. The Y-axis represents the percentage hemolysis inhibition, as further described in the text. The X-axis represents the concentration of monoclonal antibodies.

FIG. 5 shows the inhibition of the binding of radioiodinated ($^{125}$I)-human C5a to purified human neutrophils. The positive control, purified recombinant human C5a (rHuC5a), inhibited the binding. An isotype-matched irrelevant monoclonal antibody did not show any effect. The Y-axis represents the percentage inhibition of $^{125}$I-C5a binding, as further described in the text. The X-axis represents the concentration of the competing agents.

FIG. 6 shows the binding epitope of MAb 137-26 on human C5a mapped by overlapping synthetic peptides on cellulose membrane.

FIG. 7A shows CD11b expression on human neutrophils stimulated by opsonized *E. coli* in a lepirudin anti-coagulated whole blood model. Anti-C5/C5a MAb137-26 (closed circles) inhibited CD11b expression more effectively than anti-C5a MAb561 (Dr. Jurg Kohl, closed squares) and anti-C5 MAb137-30 (closed triangles). The latter antibody inhibited C5 activation. The irrelevant MAb (closed inverted triangles) had no effect. The Y-axis represents mean fluorescence intensity (MFI) measured by immunofluorocytometry. The X-axis represents the concentration of the antibodies (μg/ml) T–0=baseline whole blood sample at time 0 min. T-10=whole blood incubated only with PBS for 10 min without *E. coli*. Other samples, with or without inhibitors, had *E. coli* added.

Figure 8:
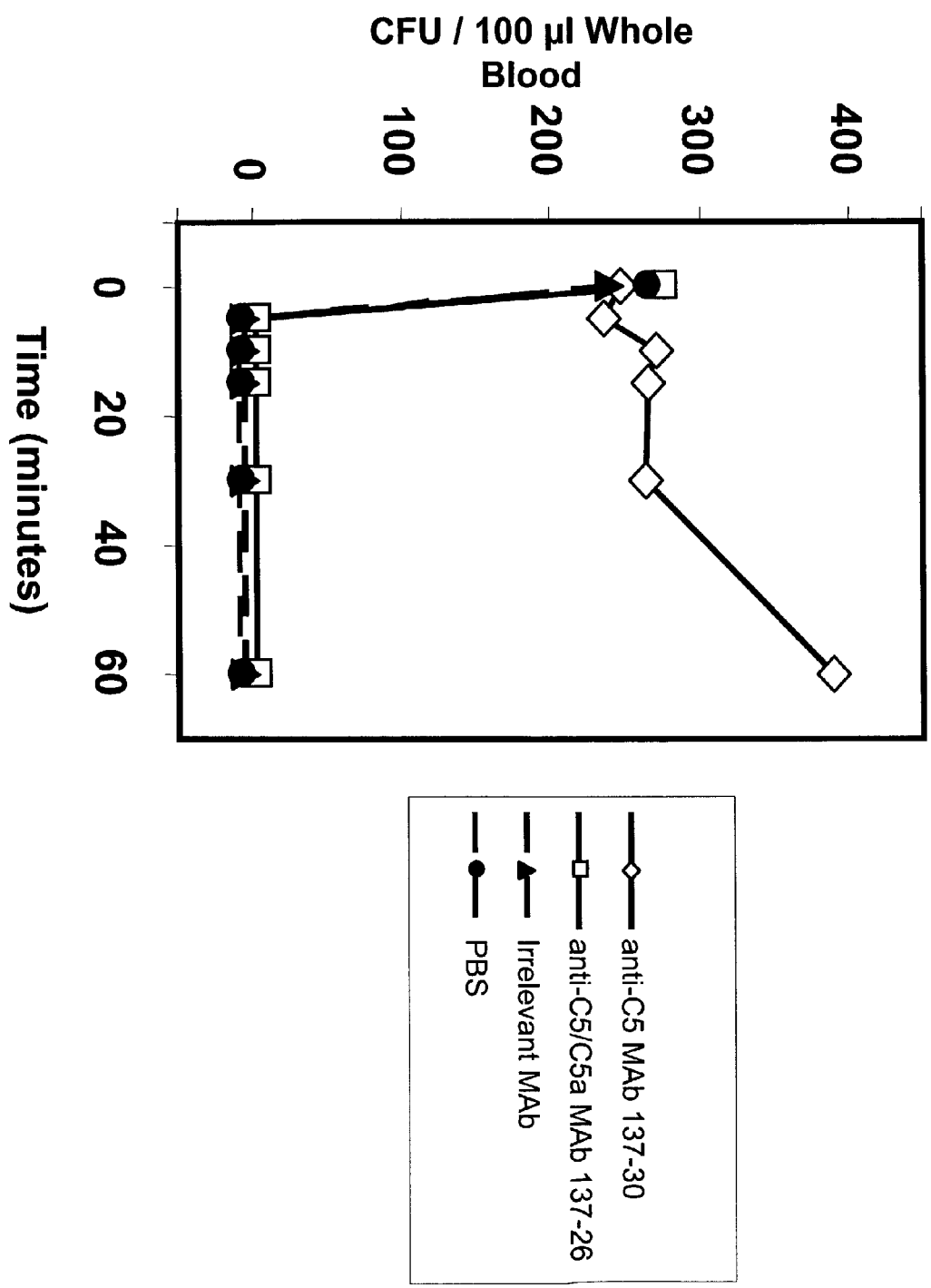

FIG. 7B shows CD11 b expression on human neutrophils stimulated by opsonized *E. coli* in a lepirudin anti-coagulated whole blood model. Anti-C5/C5a MAb 137-26 (closed circles) inhibited CD11 b expression more effectively than a peptidic C5aR antagonist (Dr. Stephen Taylor) (closed squares). The irrelevant peptide had no effec (closed inverted triangles). The Y-axis represents mean fluorescence intensity (MFI) measured by immunofluorocytometry. The X-axis represents the concentration of the antibodies/peptide (μg/ml). T-0=baseline whole blood sample at time 0 min. T-10=whole blood incubated only with PBS for 10 min without *E. coli*. Other samples, with or without inhibitors, had *E. coli* added.

FIG. 7C shows oxidative burst of human neutrophils stimulated by opsonized *E. coli* in a lepirudin ant-coagulated whole blood model. Both anti-C5/C5a MAb137-26 (closed circles) and anti-C5 MAb137-30 (closed triangles) inhibited oxidative burst more effectively than anti-C5a MAb561 (closed squares). The irrelevant antibody (closed inverted triangles) had no effect. The Y-axis represents mean fluorescence intensity (MFI) measured by immunofluorocytometry. The X-axis represents the concentration of the antibodies (μg/ml). T-0=baseline whole blood sample at time 0 min. T-10=whole blood incubated only with PBS for 10 min without *E. coli*. Other samples, with or without inhibitors, had *E. coli* added.

FIG. 7D shows oxidative burst of human neutrophils stimulated by opsonized *E. coli* in a lepirudin ant-coagulated whole blood model. Anti-C5/C5a MAb137-26 was more effective than a peptidic C5aR antagonist (closed square) in inhibiting oxidative burst. The irrelevant peptide had no effect. The Y-axis represents mean fluorescence intensity (MFI) measured by immunofluorocytometry. The X-axis represents the concentration of the antibodies in nM. T-0=baseline whole blood sample at time 0 min. T-10=whole blood incubated only with PBS for 10 min without *E. coli*. Other samples, with or without inhibitors, had *E. coli* added.

FIG. 8 shows the MAC-mediated killing of *Neisseria meningitides* in a lepirudin anti-coagulated whole blood model. The bacteria were effectively killed by incubation with the human whole blood in the presence of anti-C5/C5a MAb137-26 (closed circles), an irrelevant MAb (closed triangles), or PBS (open squares). In contrast, the bacteria were not killed when the whole blood was treated with anti-C5 MAb137-30 (open diamonds) which inhibited C5 activation and thus MAC formation. The Y-axis represents colony forming units (CFU) per 100 μl of whole blood incubated for 24 hours at 37° C. on blood agar. The X-axis represents different time points of blood sample collection from the whole blood culture experiment.

DETAILED DESCRIPTION

1. Advantages of the Invention

The inhibitors of the invention, including monoclonal antibody MAb137-26, are advantageous over known monoclonal antibody inhibitors for treating complement-mediated inflammation and tissue damage. MAb 137-26 is capable of binding to C5 before it is activated. After C5 is activated to form C5a, the antibody can neutralize C5a, which is an anaphylatoxin. Normally, once C5a is formed, it rapidly binds to C5aR on cells, thereby triggering the signal transduction cascade leading to inflammation. MAb137-26 does not inhibit the cleavage of C5 to form C5a and C5b, but C5a remains bound to MAb37-26 after it is produced, and inhibits binding of C5a to C5aR. The formation of C5b-9, however, is not affected, and, inasmuch as C5b-9 is needed for MAC formation, which is involved in killing bacteria, maintaining production of C5b-9 is important for a protective immune response.

MAb 137-26 can effectively neutralize the inflammatory effects of C5a, but still allow other components of the complement cascade, including C3 and C5b-9, to mediate anti-bacterial functions. This pharmacological property is exceptionally important with respect to the treatment of bacterial sepsis, chronic IC diseases, and psoriasis.

2. Making and Using the Invention

A. Monoclonal Antibodies

Monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal is immunized as hereinabove described to elicit lymphocytes that produce or are capable of producing antibodies that will specifically bind to the protein used for immunization. Animals can also be immunized with DNA constructs to express the encoding proteins in vivo for inducing specific antibodies. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these myeloma cell lines are murine myeloma lines, such as those derived from MOPC-21 and MPC-1 1 mouse tumors available from the Salk Institute Cell Distribution Center, San Diego, Calif. USA, and SP2/0 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.* 133:3001 (1984); Brodeur et al., *Monoclonal Antibody Production Techniques and Applications,* pp. 51-63 (Marcel Dekker, Inc., New York, 1987)). The mouse myeloma cell line NSO may also be used (European Collection of Cell Cultures, Salisbury, Wiltshire UK).

Culture medium in which hybridoma cells are grown is assayed for production of monoclonal antibodies directed against the antigen. The binding specificity of monoclonal antibodies produced by hybridoma cells may be determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI -1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (Innis M. et al. in *PCR Protocols. A Guide to Methods and Applications*, Academic, San Diego, Calif. (1990), Sanger, F. S, et al. *Proc. Nat. Acad. Sci.* 74:5463-5467 (1977)). The hybridoma cells serve as a source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty, et al., *Nature* 348: 552-554 (1990). Clackson, et al., *Nature* 352:624-628 (1991) and Marks, et al., *J. Mol. Biol.* 222:581-597 (1991) describe the isolation of murine and human antibodies, respectively, using phage libraries. Subsequent publications describe the production of high affinity (nM range) human antibodies by chain shuffling (Marks, et al., *Bio/Technology* 10:779-783 (1992)), as well as combinatorial infection and in vivo recombination as a strategy for constructing very large phage libraries (Waterhouse, et al., *Nuc. Acids. Res.* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Nat. Acad. Sci.* USA 81:6851 (1984)), or by covalently joining to the immunoglobulin coding sequence all or part of the coding sequence for a non-immunoglobulin polypeptide.

Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Another alternative is to use electrical fusion rather than chemical fusion to form hybridomas. This technique is well established. Instead of fusion, one can also transform a B-cell to make it immortal using, for example, an Epstein Barr Virus, or a transforming gene. (See, e.g., "Continuously Proliferating Human Cell Lines Synthesizing Antibody of Predetermined Specificity," Zurawaki, V. R. et al, in *Monoclonal Antibodies*, ed. by Kennett R. H. et al, Plenum Press, N.Y. 1980, pp 19-33.)

B. Humanized and Human Antibodies

A humanized antibody has one or more amino acid residues introduced into it from a source, which is non-human. These non-human amino acid residues are often referred to as "import" residues, which are typically taken from an "import" variable domain. Humanization can be essentially performed following the method of Winter and co-workers (Jones et al., *Nature* 321:522-525 (1986); Riechmann et al., *Nature* 332:323-327 (1988); Verhoeyen, et al., *Science*, 239: 1534-1536 (1988)), by substituting rodent CDRs or CDR sequences for the corresponding sequences of a human antibody. Accordingly, in such "humanized" antibodies, a substantially less than intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, the skilled researcher can produce transgenic animals (e.g., mice) that are capable, upon immunization, of producing a full repertoire of human antibodies in the absence of endogenous immunoglobulin production. Such transgenic mice are available from Abgenix, Inc., Fremont, Calif., and Medarex, Inc., Annandale, N.J. It has been described that the homozygous deletion of the antibody heavychain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA* 90:2551 (1993); Jakobovits et al., *Nature* 362:255-258 (1993); Bruggermann et al., *Year in Immunol.* 7:33 (1993);

and Duchosal et al. *Nature* 355:258 (1992). Human antibodies can also be derived from phage-display libraries (Hoogenboom et al., *J. Mol. Biol.* 227:381 (1991); Marks et al., *J. Mol. Biol.* 222:581-597 (1991); Vaughan, et al., *Nature Biotech* 14:309 (1996)).

C. DeImmunised™ Antibodies

DeImmunised™ antibodies are antibodies in which the potential T cell epitopes have been eliminated, as described in International Patent Application PCT/GB98/01473. Therefore, immunogenicity in humans is expected to be eliminated or substantially reduced when they are applied in vivo.

Additionally, antibodies can be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546, which are all hereby incorporated by reference in their entireties. Preferred polymers are polyoxyethylated polyols and polyethylene glycol (PEG). PEG is soluble in water at room temperature and has a preferred average molecular weight between 1000 and 40,000, more preferably between 2000 and 20,000, most preferably between 3,000 and 12,000.

D. Generation of Anti-C5/C5a MAbs

Antibodies of the present invention may be generated by traditional hybridoma techniques well known in the art. Briefly, mice are immunized with C5 purified from human sera as an immunogen emulsified in complete Freund's adjuvant, and injected subcutaneously or intraperitoneally in amounts ranging from 10-100 µg. Ten to fifteen days later, the immunized animals are boosted with additional C5 emulsified in incomplete Freund's adjuvant. Mice are periodically boosted thereafter on a weekly to bi-weekly immunization schedule.

For each fusion, single cell suspensions were prepared from the spleen of an immunized mouse and used for fusion with SP2/0 myeloma cells. SP2/0 cells ($1 \times 10^8$) and spleen cells ($1 \times 10^8$) were fused in a medium containing 50% polyethylene glycol (M.W. 1450) (Kodak, Rochester, N.Y.) and 5% dimethylsulfoxide (Sigma Chemical Co., St. Louis, Mo.). The cells were then adjusted to a concentration of $1.7 \times 10^5$ spleen cells/ml of the suspension in DMEM medium (Gibco, Grand Island, N.Y.), supplemented with 5% fetal bovine serum and HAT (10 mM sodium hypoxanthine, 40 µM aminopterin, and 1.6 mM thymidine). Two hundred and fifty microliters of the cell suspension were added to each well of about fifty 96-well microtest plates. After about ten days culture supernatants were withdrawn for screening for reactivity with purified human C5 by ELISA.

Wells of Immulon II (Dynatech Laboratories, Chantilly, Va.) microtest plates were coated overnight with human C5 at 0.1 µg/ml (50 µl/well). The non-specific binding sites in the wells were then saturated by incubation with 200 µl of 5% BLOTTO (non-fat dry milk) in phosphate-buffered saline (PBS) for one hour. The wells were then washed with PBST buffer (PBS containing 0.05% TWEEN®20). Fifty microliters of culture supernatant from each fusion well were added to the coated well together with 50 µl of BLOTTO for one hour at room temperature. The wells were washed with PBST. The bound antibodies were then detected by reaction with diluted horseradish peroxidase (HRP) conjugated goat anti-mouse IgG (Fc specific) (Jackson ImmunoResearch Laboratories, West Grove, Pa.) for one hour at room temperature. The wells were then washed with PBST. Peroxidase substrate solution containing 0.1% 3,3,5,5, tetramethyl benzidine (Sigma, St. Louis, Mo.) and 0.003% hydrogen peroxide (Sigma, St. Louis, Mo.) in 0.1 M sodium acetate pH 6.0 was added to the wells for color development for 30 minutes. The reaction was terminated by addition of 50 µl of 2M $H_2SO_4$ per well. The optical density (OD) was read at 450 nm with an ELISA reader (Dynatech Laboratories, Chantilly, Va.).

Hybridomas in wells positive for C5 reactivity were single-cell cloned by a limiting dilution method. Monoclonal hybridomas were then expanded and culture supernatants collected for purification by protein A chromatography. The purified antibodies were then characterized for reactivity with human C5 and C5a by ELISA, for determination of affinity and kinetic binding constants by BIAcore, for effects on complement-mediated hemolysis via both the classical and the alternative pathways, and for inhibition of $^{125}$I-C5a binding to purified human neutrophils.

Antibodies may also be selected by panning a library of human scFv for those which bind C5 (Griffiths et. al., EMBO J. 12:725-734 (1993)). The specificity and activity of specific clones can be assessed using known assays (Griffiths et. al.; Clarkson et. al., *Nature*, 352: 642-648 (1991)). After a first panning step, one obtains a library of phage containing a plurality of different single chain antibodies displayed on phage having improved binding for C5. Subsequent panning steps provide additional libraries with higher binding affinities. When avidity effects are a problem, monovalent phage display libraries may be used in which less than 20%, less than 10%, or less than 1% of the phage display more than one copy of an antibody on the surface of the phage. Monovalent display can be accomplished with the use of phagemid and helper phage. Suitable phage include M13, fl and fd filamentous phage. Fusion protein display with virus coat proteins is also known and may be used in this invention. MAb137-26, which binds both C5 and C5a with comparable affinity, was further characterized. MAb 137-26 does not inhibit C5 activation, but inhibits with very high potency the binding of C5a to C5aR on purified human neutrophils. Experiments demonstrating these properties are further explained in the Examples below.

To screen for antibodies which bind to a particular epitope on the antigen of interest (e.g., those which block binding of any of the antibodies disclosed herein to C5), a routine cross-blocking assay such as that described in Antibodies, A Laboratory Manual, Cold Spring Harbor Laboratory, Ed Harlow and David Lane (1988), can be performed. Alternatively, epitope mapping, e.g. as described in Champe et al., *J. Biol. Chem.* 270:1388-1394 (1995), can be performed to determine whether the antibody binds an epitope of interest.

E. Making Other Inhibitors of the Invention

Other molecules suitable for use in the invention can be isolated or screened from compound libraries by conventional means, for example, by determining whether they bind to C5/C5a, and then doing a functional screen to determine if they inhibit the activity of C5b. An automated system for generating and screening a compound library is described in U.S. Pat. Nos. 5,901,069 and 5,463,564. More focused approaches involve a competitive screen against the MAb 137-26, or making a three-dimensional model of the binding site, and then making a family of molecules, which fit the model. These are then screened for those with optimal binding characteristics. In addition, other molecules may be identified by competition assay, or a functional screen for inhibitors with the same properties as MAb137-26.

F. Using the Inhibitors of the Invention

The molecules of the present invention can be administered by any of a number of routes and are administered at a concentration that is therapeutically effective in the indication or for the purpose sought. To accomplish this goal, the antibodies may be formulated using a variety of acceptable excipients known in the art. Typically, the antibodies are administered by injection. Methods to accomplish this administration are known to those of ordinary skill in the art. It may also be possible to obtain compositions which may be topically or orally administered, or which may be capable of transmission across mucous membranes.

The dosage and mode of administration will depend on the individual and the agent to be administered. The dosage can be determined by routine experimentation in clinical trials or extrapolation from animal models in which the antibody was effective.

The antibodies of the present invention may be used in the treatment of diseases and conditions mediated by excessive or uncontrolled production of C5a. Evidence of the utility of the inhibitors of the invention in treating these diseases and conditions is set forth below.

EXAMPLE 1

Reactivity of MAb137-26 with Human C5 and C5a

MAb 137-26 was tested for reactivity with purified human C5 and recombinant C5a (Sigma, St. Louis, Mo.). The procedures of the ELISA are described above. MAb 137-26 binds to C5a in a dose-dependent manner with high potency (FIG. 1). Another anti-C5 MAb 137-76, specific for the β-chain of human C5, does not bind C5a, because C5a resides on the a-chain of C5. An isotype-matched irrelevant antibody used as a negative control also does not react with C5a. On the other hand, both MAbs 137-26 and 137-76 bind to C5 (FIG. 2).

The affinity equilibrium constant and the binding kinetic constants (association and dissociation) of MAb 137-26 with C5a and C5 were also determined by a BIAcore instrument (Pharmacia Biosensor AB, Uppsala, Sweden). All the binding measurements were performed in HEPES-buffered saline (HBS) (10 mM HEPES, pH 7.4, 150 mM NaCl, 3.4 mM EDTA, 0.005% Surfactant P20) at 25° C. To measure the binding rate constants of C5 and C5a to MAb137-26, rabbit anti-mouse IgG(Fc) antibodies were immobilized onto a CM5 sensorchip by amine coupling using N-hydroxysuccinimide and N-ethyl-N'-(3-diethylaminopropyl)carbodiimide. MAb137-26 was then captured onto the coated sensorchip before the injection of C5 at different concentrations. The data are summarized in Table 1. MAb137-26 has a high binding affinity for both solution-phase C5a and C5. The results also indicate that MAb 137-26 binds to an epitope shared by both C5a and C5.

TABLE 1

Kinetic Constants of C5 and C5a Binding to MAb137-26

|     | $k_{on}$ $(M^{-1}s^{-1})$ | $k_{off}$ $(s^{-1})$ | $K_D$ (M) |
| --- | --- | --- | --- |
| C5  | $1.42 \times 10^5$ | $6.97 \times 10^{-5}$ | $4.92 \times 10^{-10}$ |
| C5a | $3.7 \times 10^6$ | $2.25 \times 10^{-4}$ | $6.09 \times 10^{-11}$ |

$k_{on}$, kinetic association constant
$k_{off}$, kinetic dissociation constant
$K_D$, equilibrium dissociation constant = $k_{off}/k_{on}$

EXAMPLE 2

Complement-Mediated Hemolysis

To study the effects of MAb 137-26 on the activation of C5 in human serum, the antibody was tested for inhibition of hemolysis mediated by the classical and the alternative complement pathways.

For the classical pathway experiments, chicken RBCs ($5 \times 10^7$ cells/ml) in gelatin/veronal buffered saline (GVB$^{++}$) containing 0.5 mM MgCl$_2$ and 0.15 mM CaCl$_2$ were sensitized with purified rabbit anti-chicken RBC immunoglobulins at 8 μg/ml (Inter-Cell Technologies, Hoperwell, N.J.) for 15 minutes at 4° C. The cells were then washed with GVB$^{++}$. The washed cells were re-suspended in the same buffer at $1.7 \times 10^8$ cells/mi. In each well of a round-bottom 96-well microtest plate, 50 μl of normal human serum (5.2%) was mixed with 50 μl of GVB$^{++}$ of serially diluted MAb137-26 or an anti-C2 MAb 175-62 as a positive control. Then 30 μl of the washed sensitized chicken RBCs suspension was added to the wells containing the mixtures. Fifty microliters of normal human serum (5.2%) was mixed with 80 μl of GVB$^{++}$ to give the serum color background. An isotype-matched anti-HIV-1 gp120 MAb was used as negative control. The final human serum concentration used was 2%. The mixture was incubated at 37° C. for 30 minutes. The plate was shaken on a microtest plate shaker for 15 seconds. The plate was then centrifuged at 300×g for 3 minutes. Supernatants (80 μl) were collected and transferred to wells in a flat-bottom 96-well microtest plates for measurement of OD at 405 nm by an ELISA plate reader. The percent inhibition of hemolysis is defined as:

$$100 \times [(OD_{without\ MAb} - OD_{serum\ color\ background}) - (OD_{with\ MAb} - OD_{serum\ color\ background})] / (OD_{without\ MAb} - OD_{serum\ color\ background}).$$

FIG. 3 shows that MAb137-26 and the irrelevant control MAb G3-519 do not inhibit the classical pathway hemolysis of sensitized chicken RBCs, whereas the positive control, anti-C2 MAb 175-62, effectively inhibits hemolysis. C2 is specifically involved in the classical complement pathway.

For the alternative pathway, unsensitized rabbit RBCs were washed three times with gelatin/veronal-buffered saline (GVB/Mg-EGTA) containing 2 mM MgCl$_2$ and 1.6 mM EGTA. EGTA at a concentration of 10 mM was used to inhibit the classical pathway (K. Whaley et al., in A. W. Dodds (Ed.), Complement: A Practical Approach. Oxford University Press, Oxford, 1997, pp. 19-47). The assay procedures are similar to those of the classical pathway hemolysis assay described above. The final concentration of human serum used in the assay was 10%. Anti-factor D MAb 166-32 was used as positive control. The same isotype-matched irrelevant anti-HIV-1 gp120 MAb described above was used as negative control.

FIG. 4 shows that MAb137-26 does not inhibit the alternative pathway hemolysis of unsensitized rabbit RBCs, whereas anti-factor D MAb166-32 strongly inhibits the hemolysis. Factor D is specific for the alternative complement pathway. The negative control antibody has no effect.

Taken together, the results verify that MAb 137-26 does not inhibit C5 activation, and therefore the formation of C5a and C5b-9 are not inhibited. MAb137-26 does not inhibit the activation of the alternative and classical complement pathways.

EXAMPLE 3

Inhibition of $^{125}$I-C5a Binding to Purified Human Neutrophils by MAb 137-26

Human neutrophils were purified from human whole blood and diluted with Dextran T-500/saline solution. The mixture was incubated at room temperature for about 20 minutes or until a clearly defined surface layer appeared. This surface layer was transferred to a 50-ml polypropylene centrifuge tube. Following centrifugation, the cell pellet was suspended in 30 ml of cold PBSB (1% BSA in PBS). The cell suspension was layered on top of 10 ml of Histopaque-1077 (Sigma, St. Louis, Mo.) in a 50-ml polypropylene centrifuge tube. Following another centrifugation, the cell pellet was then re-suspended in 20 ml of cold 0.2% NaCl for 30 seconds to lyse RBCs. Then, 20 ml of cold 1.6% NaCl were added to the cell suspension, recentrifuged, and the neutrophils were resuspended in PBSB. The neutrophils were kept on ice until being used for $^{125}$I-C5a binding.

MAb137-26 was serially diluted in 1.5 ml Eppendorf centrifuged tubes with a binding buffer (1% BSA in RPMI1640 medium) to give final concentrations ranging from 640 nM to 0.04 nM. Four microliters of 4 nM $^{125}$I-C5a (NEN Life Science Products, Inc., Boston, Mass.) were added to 36 µl of diluted MAb 137-26 for incubation at room temperature for 15 minutes. Purified recombinant human C5a (Sigma, St. Louis, Mo. was used as positive control, whereas an isotype-matched irrelevant monoclonal antibody was used as negative control. For the maximum binding of $^{125}$I-C5a, 36 µl of the binding buffer without the antibodies or C5a was used instead. Fifty microliters of the neutrophil suspension was added to each tube for incubation on ice. At the end of the 40-minute incubation period, the mixture from each tube was transferred to the top of 800 µl of a separation buffer (6% BSA in PBS) in another Eppendorf tube. The tubes were than centrifuged at 2000×g for 3 minutes at room temperature. After the supernatant was aspirated, the cell pellet was re-suspended in 0.5 ml of de-ionized water to lyse the cells. The cell lysate was then mixed with 3 ml of Ultima Gold scintillation fluid (Packard Instrument, Meriden, Conn.) for radioactive counting. The percent inhibition of $^{125}$I-C5a binding is defined as:

$$[Cpm_{max}-Cpm_{bkg}]-[Cpm_{ca}-Cpm_{bkg}]/[Cpm_{max}-Cpm_{bkg}]\times 100$$

where:

$Cpm_{max}$=maximum count per minute without competing agents;
$Cpm_{bkg}$=background cpm without addition of $^{125}$I-C5a; and
$Cpm_{ca}$=cpm with competing agents.

FIG. 5 shows the inhibition of the binding of radioiodinated ($^{125}$I)-human C5a to purified human neutrophils. MAb 137-26 is more potent than unlabeled C5a in inhibiting the binding of $^{125}$I-C5a to purified human neutrophils. The dose for 50% inhibition (ID50) for MAb 137-26 was 0.45 nM as compared to 30 nM C5a.

EXAMPLE 4

Mapping of the Binding Epitope of MAb137-26 on Human C5a by SPOTs Peptides on Cellulose Membrane The binding epitope of MAb 137-26 on human C5a was mapped by a technique using SPOTs peptides synthesized by Sigma Genosys (the Woodlands, Tex.). Overlapping peptides (12-mer) encompassing the entire human C5a were synthesized on a cellulose membrane. In the assay, the membrane was first treated with a blocking solution TBSTB (10 mM Tris chloride, 250 mM sodium chloride, 1% bovine serum albumin and 0.05% TWEEN® 20) for 1 hour at room temperature to saturate all the non-specific binding sites. MAb 136-26 at 1 µtg/ml in the blocking solution was then added to the membrane for 1 hour at room temperature. The membrane was then washed thoroughly with a washing buffer TBST (10 mM Tris chloride, 250 mM sodium chloride and 0.05% TWEEN® 20). The membrane was then treated with HRP-conjugated goat anti-mouse IgG (Fc) antibody (diluted 1:5,000 in the blocking buffer) (Jackson immunoresearch, West Grove, Pa.) for 1 hour at room temperature. The membrane was then washed again. The binding of MAb137-26 to the individual SPOTs peptides of C5a was detected by incubation with Supersignal West Pico chemilluminescent substrate (Pierce, Rockford, Ill.). The intensity of chemillumescence was then detected by exposure to Kodak X-OMAT AR film (Rochester, N.Y.). FIG. 6 shows the sequence of the epitope bound by MAb 137-26.

EXAMPLE 5

An ex vivo Human Whole Blood Model for Studying Complement-mediated Inflammation: Effect of MAb137-26 on Neutrophil Activation by E. coli and on Killing of Neisseria Meningitidis In order to investigate the role of complement in the complex inflammatory network, all potential cellular and fluid-phase mediators need to be present and therefore are able to interact simultaneously. For devising such an experiment condition in vitro, human whole blood was used. In this model, lepirudin (REFLUDAN®), a thrombin specific hirudin analogue, was used as an anticoagulant instead of heparin. Unlike heparin, lepirudin does not interfere with complement activation.

In this model system, MAb 137-26 blocked the inflammatory effects of C5a formed as a result of complement activation by E. coli. The antibody did not inhibit MAC-mediated killing of N. meningitidis. Therefore, MAb137-26 neutralizes C5a without inhibiting C5 activation and the subsequent formation of MAC. This is an important feature of the monoclonal antibodies of the present invention.

Whole blood was collected in polypropylene tubes containing lepirudin (50 µg/ml). The anti-coagulated whole blood was pre-incubated with PBS or anti-C5 inhibitors for 4 minutes at 37° C. For the studies of CD11b expression and oxidative burst on neutrophils, opsonized E. coli strain LE392 (ATCC 33572) was added to the whole blood samples for 10 minutes at 37° C. The E. coli concentration was $1\times10^7$/ml blood in the CD11b experiments and $1\times10^8$/ml in the oxidative burst experiments. The T–0 baseline sample was processed immediately. After incubation, 100 µof samples was used for measurement of CD1b expression on neutrophils by immunofluorocytometry. The oxidative burst of activated neutrophils was measured using the substrate dihydrorhodamine 123 and performed as described in the Burst-test procedure (ORPEGEN Pharma, Heidelberg, Germany).

FIGS. 7A-7D depict the results of the flow cytometric assays of neutrophil activation for CD11b expression and oxidative burst. Anti-C5/C5a MAb137-26 inhibited effectively neutrophil activation induced by E. coli in the human whole blood model of inflammation. In these assays, MAb137-26 is more potent than anti-C5a MAb561 (Dr. Jurg Kohl) and a peptidic C5aR antagonist (Dr. Stephen Taylor)

For the bactericidal assays, *N. meningitidis* H44/76-1 was grown overnight on BHI-agar, subcultured and grown into log-phase for 4 hours. 5000-10000 colony forming units (CFUs) were added to 1.1 ml of lepirudin anti-coagulated whole blood samples preincubated for 5 minutes with PBS or antibody. At each time period, 100 μl of whole blood was seeded on microbiological Petri dishes containing blood agar and incubated for 24 hours at 37° C. Bacterial growth was expressed as CFU/100 μl of whole blood added. T−0 sample was obtained immediately after adding the bacteria.

FIG. 8 show that MAb137-26 did not inhibit MAC-mediated killing of *Neisseria meningitides*. In contrast, MAb137-30 inhibited the killing of *Neisseria meningitides* by human whole blood. This antibody inhibits C5 activation.

It should be understood that the terms and expressions used in the foregoing sections are exemplary only and not limiting, and that the scope of the invention is defined only in the claims which follow, and includes all equivalents of the subject matter of those claims.

We claim:

1. An isolated antibody or antigen binding fragment thereof that binds to human C5 and C5a, but does not prevent the activation of C5 and does not prevent formation of or inhibit the activity of C5b.

2. The antibody or antigen binding fragment of claim 1, wherein the antibody binds to free C5a with equal or better affinity than to C5.

3. The antibody or antigen binding fragment of claim 1, wherein the antibody inhibits the binding of C5a to C5aR.

4. An isolated antibody or antigen binding fragment thereof that blocks the binding of monoclonal antibody 137-26 produced from the hybridoma deposited with the ATCC and designated PTA-3650 to human C5.

5. The antibody or antigen binding fragment thereof of claim 1, wherein the antibody is a monoclonal antibody.

6. The antibody or antigen binding fragment thereof of claim 1, wherein the fragment is selected from the group consisting of Fab, $F(ab')_2$, Fv, and single chain Fv.

7. The antibody or antigen binding fragment thereof of claim 5, wherein the antibody is a chimeric, deimmunized, humanized or a human antibody.

8. A composition comprising the antibody or antigen binding fragment of claim 1 or claim 4 and a pharmacologically acceptable carrier, excipient, stabilizer, or diluent.

9. A diagnostic method comprising the detection of the amount of C5 or C5a present in a sample with the antibody or antigen binding fragment of claim 1 or claim 4.

10. The diagnostic method of claim 9, wherein the antibody is the monoclonal antibody 137-26 produced from the hybridoma deposited with the ATCC and designated PTA-3650.

11. The monoclonal antibody 137-26 produced from the hybridoma deposited with the ATCC and designated PTA-3650.

12. The hybridoma cell line designated PTA-3650.

* * * * *